(12) United States Patent
Zhuravsky

(10) Patent No.: US 6,394,516 B1
(45) Date of Patent: May 28, 2002

(54) UTENSIL HOLDING DEVICE

(76) Inventor: Alexander Zhuravsky, 2279 E. 22nd St., Brooklyn, NY (US) 11229

( * ) Notice: Subject to any disclaimer, the term of this patent is extended or adjusted under 35 U.S.C. 154(b) by 0 days.

(21) Appl. No.: 09/735,351

(22) Filed: Dec. 13, 2000

(51) Int. Cl.[7] ............................. A61F 2/78; B25J 1/00
(52) U.S. Cl. ......................... 294/25; 224/218; 623/65
(58) Field of Search ............................ 294/25; 2/159, 2/160; 30/298, 323, 327; 224/217–219, 221; 623/65

(56) References Cited

U.S. PATENT DOCUMENTS

| | | | | |
|---|---|---|---|---|
| 1,369,326 A | * | 2/1921 | Cottman | 30/298 |
| 2,889,160 A | * | 6/1959 | Nelson | 294/25 X |
| 3,358,527 A | * | 12/1967 | Lake et al. | 294/25 X |
| 3,981,526 A | * | 9/1976 | Lundqvist | 294/25 |
| 4,157,616 A | * | 6/1979 | Lundqvist | 294/25 X |
| 4,447,912 A | * | 5/1984 | Morrow | 2/160 X |
| 5,597,189 A | * | 1/1997 | Barbee | 294/25 |
| 5,779,292 A | * | 7/1998 | Kasday | 294/25 |
| 5,853,210 A | * | 12/1998 | Robinson | 294/25 |

* cited by examiner

Primary Examiner—Johnny D. Cherry
(74) Attorney, Agent, or Firm—Goldstein Law Offices, P.C.

(57) ABSTRACT

A utensil holding device including a support portion adapted for coupling with the hand and wrist of a user. A utensil holding portion is secured to the support portion.

3 Claims, 2 Drawing Sheets

UTENSIL HOLDING DEVICE

BACKGROUND OF THE INVENTION

The present invention relates to a utensil holding device and more particularly pertains to allowing people with limited or no use of their hands to perform tasks with various implements and utensils.

Many people, whether due to arthritis or other disabling condition, have limited, or no use of their hands. This causes a problem when these people need to perform the most basic functions, such as eating and brushing their teeth. Their condition limits their ability to handle the implements that are normally associated with these functions. Additionally, some people have problems with their wrists in addition to the conditions that affect their hands. What is needed is a device that will allow people to easily handle utensils and other implements while at the same time provide support to the wrist so that a person can effectively wield said utensils and other implements.

The present invention attempts to solve the abovementioned problems by providing a device that allows a person to hold a utensil or implements in their hands while at the same time supporting their wrist.

The use of aids for disabled persons is known in the prior art. More specifically, aids for disabled persons heretofore devised and utilized for the purpose of allowing disabled persons to handle items are known to consist basically of familiar, expected and obvious structural configurations, notwithstanding the myriad of designs encompassed by the crowded prior art which have been developed for the fulfillment of countless objectives and requirements.

By way of example, U.S. Pat. No. 4,165,896 to Hunt discloses an instrument holder comprises of a hand encircling band for use by a user without function of their hands. U.S. Pat. No. 3,942,194 to Winter and U.S. Pat. No. 4,606,484, also to Winter, disclose additional devices to allow a person with limited use of his or her hands to use implements such as a knife, fork or toothbrush. U.S. Pat. No. 3,781,052 to Millington discloses a means for attaching a tool to a hand, for use in a hazardous work area.

While these devices fulfill their respective, particular objective and requirements, the aforementioned patents do not describe a utensil holding device for allowing people with limited or no use of their hands to perform tasks with various implements and utensils.

In this respect, the utensil holding device according to the present invention substantially departs from the conventional concepts and designs of the prior art, and in doing so provides an apparatus primarily developed for the purpose of allowing people with limited or no use of their hands to perform tasks with various implements and utensils.

Therefore, it can be appreciated that there exists a continuing need for a new and improved utensil holding device which can be used for allowing people with limited or no use of their hands to perform tasks with various implements and utensils. In this regard, the present invention substantially fulfills this need.

SUMMARY OF THE INVENTION

In the view of the foregoing disadvantages inherent in the known types of aids for disabled persons now present in the prior art, the present invention provides an improved utensil holding device. As such, the general purpose of the present invention, which will be described subsequently in greater detail, is to provide a new and improved utensil holding device which has all the advantages of the prior art and none of the disadvantages.

To attain this, the present invention essentially comprises a support portion adapted for coupling with the hand and wrist of a user. The support portion includes a wrist portion and a hand portion. The wrist portion receives the wrist of the user therein. The wrist portion has an upper end, a lower end, a cupped upper surface, and an arched lower surface. The cupped upper surface receives the wrist therein. The hand portion receives the hand of the user thereon. The hand portion has an upper end, a lower end, an arched upper surface, and a cupped lower surface. The lower end of the hand portion is secured to the upper end of the wrist portion. The arched upper surface of the hand portion receives the hand of the user thereon. A pair of wrist straps are secured to the wrist portion of the support portion. A pair of hand straps are secured to the hand portion of the support portion. A utensil holding portion is secured to the cupped lower surface of the hand portion of the support portion. The utensil holding portion is comprised of a hollow cylinder having an open upper end. The open upper end has a pliable washer disposed therein for receiving and engaging implements and utensils.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved utensil holding device which has all the advantages of the prior art aids for disabled persons and none of the disadvantages.

It is another object of the present invention to provide a new and improved utensil holding device which may be easily and efficiently manufactured and marketed.

It is a further object of the present invention to provide a new and improved utensil holding device which is of durable and reliable construction.

An even further object of the present invention is to provide a new and improved utensil holding device which is susceptible of a low cost of manufacture with regard to both materials and labor, and which accordingly is then susceptible of low prices of sale to the consuming public, thereby making such utensil holding device economically available to the buying public.

Even still another object of the present invention is to provide a new and improved utensil holding device for allowing people with limited or no use of their hands to perform tasks with various implements and utensils.

Lastly, it is an object of the present invention to provide a new and improved utensil holding device including a support portion adapted for coupling with the hand and wrist of a user. A utensil holding portion is secured to the support portion.

These, together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts through the various figures.

DESCRIPTION OF THE PREFERRED EMBODIMENT

Figure 1:
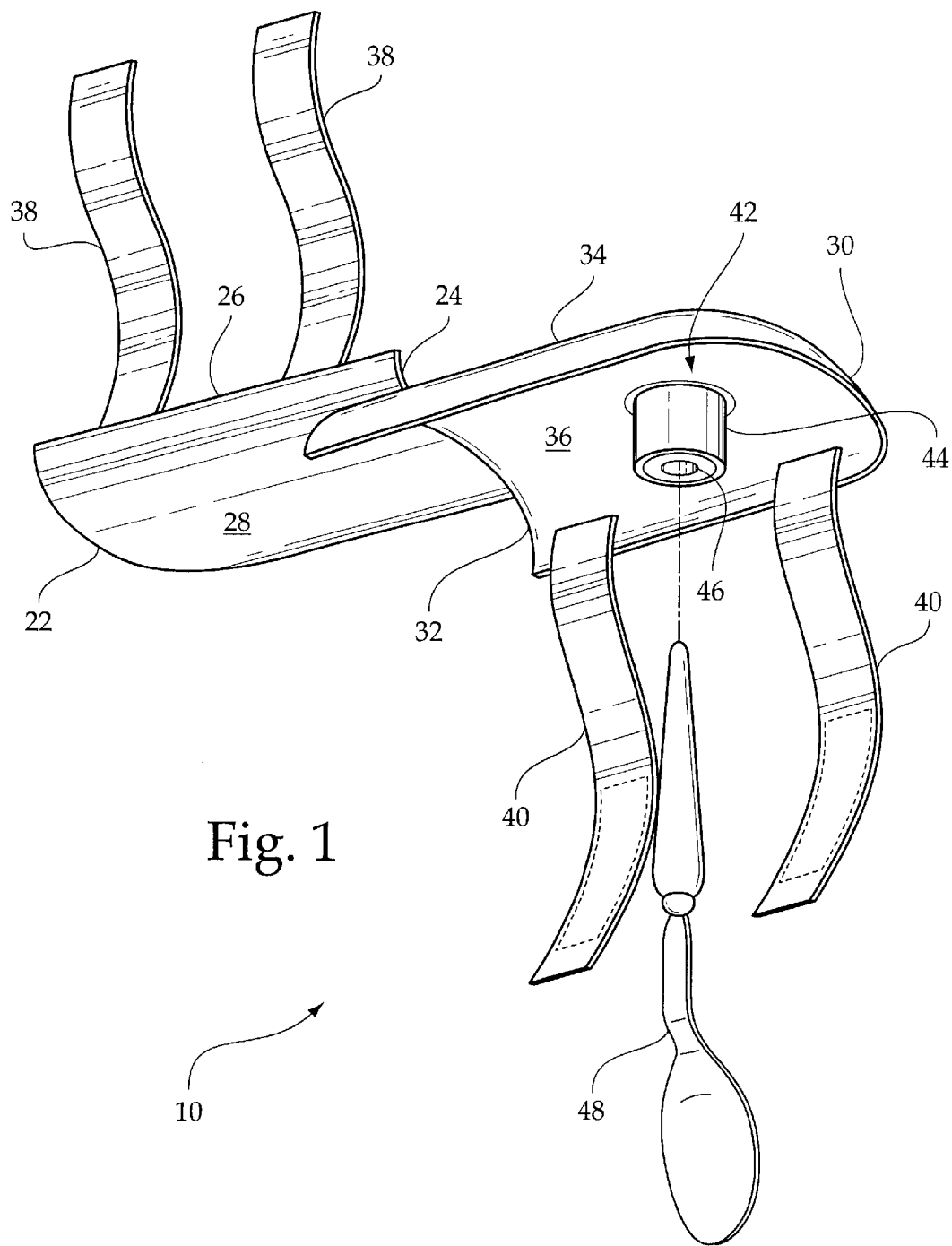
FIG. 1 is a perspective view of the preferred embodiment of the utensil holding device constructed in accordance with the principles of the present invention.
Figure 2:
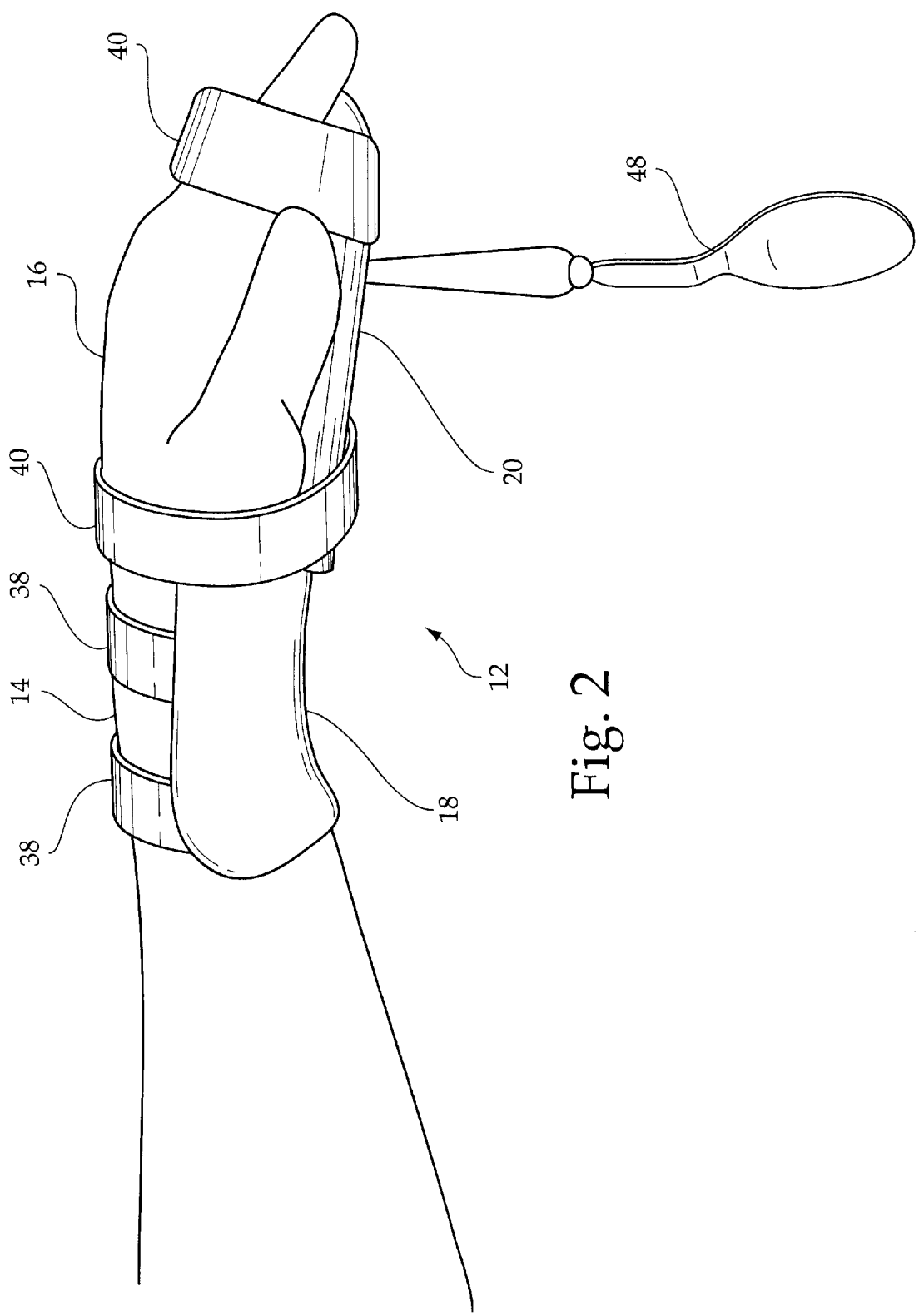
FIG. 2 is a side view of the present invention illustrated in use.

With reference now to the drawings, and in particular, to FIGS. 1 and 2 thereof, the preferred embodiment of the new and improved utensil holding device embodying the principles and concepts of the present invention and generally designated by the reference number 10 will be described.

Specifically, it will be noted in the various Figures that the device relates to a utensil holding device for allowing people with limited or no use of their hands to perform tasks with various implements and utensils. In its broadest context, the device consists of a support portion, a pair of wrist straps, a pair of hand straps, and a utensil holding portion. Such components are individually configured and correlated with respect to each other so as to attain the desired objective.

The support portion 12 is adapted for coupling with the hand 16 and wrist 14 of a user. The support portion 12 includes a wrist portion 18 and a hand portion 20. The wrist portion 18 receives the wrist 14 of the user therein. The wrist portion 18 has an upper en 24, a lower end 22, a cupped upper surface 26, and an arched lower surface 28. The cupped upper surface 26 receives the wrist 14 therein. The hand portion 20 receives the hand 16 of the user thereon. The hand portion 20 has an upper end 30, a lower end 32, an arched upper surface 34, and a cupped lower surface 36. The lower end 32 of the hand portion 20 is secured to the upper end 24 of the wrist portion 18. The arched upper surface 34 of the hand portion 20 receives the hand 16 the user thereon.

The pair of wrist straps 38 are secured to the wrist portion 18 of the support portion 12. The pair of wrist straps 38 will wrap around the user's wrist while positioned within the wrist portion 18 to secure the wrist portion 18 to the user. The wrist straps 38 will be provided with pile type fasteners of the like to facilitate securement.

The pair of hand straps 40 are secured to the hand portion 20 of the support portion 12. The hand straps 40 will wrap around the user's hand while positioned atop the hand portion 20 to secure the hand portion 20 to the user. The hand straps 40, like the wrist straps 38, will be provided with pile type fasteners or the like to facilitate securement.

The utensil holding portion 42 is secured to the cupped lower surface 36 of the hand portion 20 of the support portion 12. The utensil holding portion 42 is comprised of a hollow cylinder 44 having an open upper end. The open upper end has a pliable washer 46 disposed therein for receiving and engaging implements and utensils 48. The utensil 48 will be received endwise within the open upper end of the cylinder through the pliable washer 46. The pliable washer 46 will be able to expand to receive the utensil 48 and then retract to engage the utensil 48. In use, the utensil 48 will be projecting outwardly essentially from the palm of the hand 16 of the user. Note FIG. 2.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A utensil holding device for allowing people with limited or no use of their hands to perform tasks with various implements and utensils, the device coupling with a user's hand and wrist, the device comprising, in combination:

a support portion for use with the hand and wrist of a user, the support portion including a wrist portion and a hand portion, the wrist portion receiving the wrist of the user therein, the wrist portion having an upper end, a lower end, a cupped upper surface, and an arched lower surface, the cupped upper surface receiving the wrist therein, the hand portion receiving the hand of the user thereon, the hand portion having an upper end, a lower end, an arched upper surface, and a cupped lower surface, the lower end of the hand portion being secured to the upper end of the wrist portion, the arched upper surface of the hand portion receiving the hand of the user thereon;

a pair of wrist straps secured to the wrist portion of the support portion;

a pair of hand straps secured to the hand portion of the support portion; and a utensil holding portion secured to the cupped lower surface of the hand portion of the support portion, the utensil holding portion being comprised of a hollow cylinder having an open upper end, the open upper end having a pliable washer disposed therein for receiving and engaging implements and utensils.

2. A utensil holding device for allowing people with limited or no use of their hands to perform tasks with various implements and utensils, the device coupling with a user's hand and wrist, the device comprising, in combination:

a support portion for use with the hand and wrist of a user, the support portion including a wrist portion and a hand portion, the wrist portion receiving the wrist of the user therein, said wrist portion having an upper end, a lower end, a cupped upper surface receiving the wrist therein, and an arched lower surface, the hand portion receiving the hand of the user thereon, said hand portion having an upper end, a lower end secured to the upper end of the wrist portion, an arched upper surface receiving the hand of the user thereon, and a cupped lower surface; and a utensil holding portion secured to the support portion.

3. A utensil holding device for allowing people with limited or no use of their hands to perform tasks with various implements and utensils, the device coupling with a user's hand and wrist, the device comprising, in combination:

a support portion adapted for coupling with the hand and wrist of a user, the support portion including a wrist portion and a hand portion, the wrist portion receiving the wrist of the user therein, the hand portion receiving the hand of the user thereon; and a utensil holding portion secured to the support portion, the utensil holding portion comprising a hollow cylinder having an open upper end, the open upper end having a pliable washer disposed therein for receiving and engaging implements and utensils.

* * * * *